United States Patent [19]

Clark et al.

[11] 3,934,457
[45] Jan. 27, 1976

[54] VESSEL NOZZLE INSPECTION APPARATUS

[75] Inventors: Jack Phillip Clark; Thurman Dale Smith; Alan Carl Foster, all of San Jose, Calif.

[73] Assignee: General Electric Company, San Jose, Calif.

[22] Filed: Jan. 13, 1975

[21] Appl. No.: 540,679

[52] U.S. Cl............................. 73/67.8 S; 176/19 R
[51] Int. Cl.²......................................... G01N 29/04
[58] Field of Search............ 73/67.8 S, 67.8 R, 67.9, 73/67, 71.5 US; 176/19 R

[56] References Cited
UNITED STATES PATENTS

| | | | |
|---|---|---|---|
| 3,068,370 | 12/1962 | McInnish | 73/67.8 S |
| 3,178,933 | 4/1965 | Block | 73/67.8 S |
| 3,540,266 | 11/1970 | Lofgren | 73/67.8 S |
| 3,809,607 | 5/1974 | Murray et al. | 73/67.8 S |
| 3,844,164 | 10/1974 | Romere | 73/67.8 S |
| 3,844,165 | 10/1974 | Savoy | 73/67.8 S |

*Primary Examiner*—Richard C. Queisser
*Assistant Examiner*—Stephen A.. Kreitman
*Attorney, Agent, or Firm*—Ivor J. James, Jr.; Samuel E. Turner; Sam E. Laub

[57] ABSTRACT

Apparatus for on-site, non-destructive examination of the connection of a pipe to a vessel including a vessel-to-nozzle and nozzle-to-pipe weld seams, including an instrument carrying, remotely controlled vehicle with magnetic adherence means for scanning such connection.

24 Claims, 4 Drawing Figures

VESSEL NOZZLE INSPECTION APPARATUS

BACKGROUND

The attachment of pipes, for example, steam lines, feedwater lines and the like, to a vessel is commonly accomplished by the use of a separately formed annular sleeve or nozzle welded between the vessel and the pipe, the nozzle providing, in effect, a reinforcement of the vessel-to-pipe connection.

In some instances it is desirable to provide in-service inspection of the welds and other portions of such connections to verify their integrity or to discover any incipient defects so that appropriate repairs can be made before failure occurs.

In some cases, for example, where the vessel is relatively inaccessable or hazardous to humans, the use of conventional inspection techniques and equipment is undesirable or even impossible. A notable example is a pressure vessel containment for a nuclear reactor. Such a pressure vessel may be in the order of 60 feet in height and 20 feet in diameter with walls of steel 4 to 12 inches in thickness with a number of pipes, for example, from 4 inches to 28 inches in diameter connected thereto. In use, such a vessel and the adjacent portions of the pipes and the attachment nozzles are exposed to radioactive fields. Furthermore, such vessels are ordinarily closely surrounded (for example, as closely as 8 inches) by heat insulation and a biological shield wall. Limited access to the pipe attachment nozzles is usually provided by ports through which the pipes penetrate the shield wall, the space between the pipe and the port being normally closed by a shield door, hatch, shield blocks or the like. Thus, the foregoing conditions make it desirable to provide in-service inspection equipment which can be quickly installed and removed and which can be remotely operated to perform the desired examination. No previously known devices or equipment suitable to accomplish this purpose have been found.

It is an object of this invention to provide apparatus for the examination of the pipe attachments to a vessel which apparatus can be readily installed and removed and remotely controlled.

SUMMARY

This and other objects of the invention are achieved by an instrument carrying vehicle which travels a circular track removably secured to the attachment nozzle to be examined. The track is segmented to allow installation around and removal from the nozzle and it is removable held to the nozzle by a series of permanent magnets. The vehicle is fitted with a plurality of in-line wheels containing permanent magnets for adherence of the vehicle to the track. Secured to and extending from the vehicle frame are inner and outer arms. These arms form guides for translatable carriages to which are attached weld seam examination devices such as ultrasonic signal transducers which thus can be moved back and forth to scan the welds. Transducers carried by an intermediate carriage scan the inner radius region of the nozzle.

DRAWINGS

Other features and further details of the invention are described hereinafter with reference to the accompanying drawing wherein.

DESCRIPTION

Figure 1:
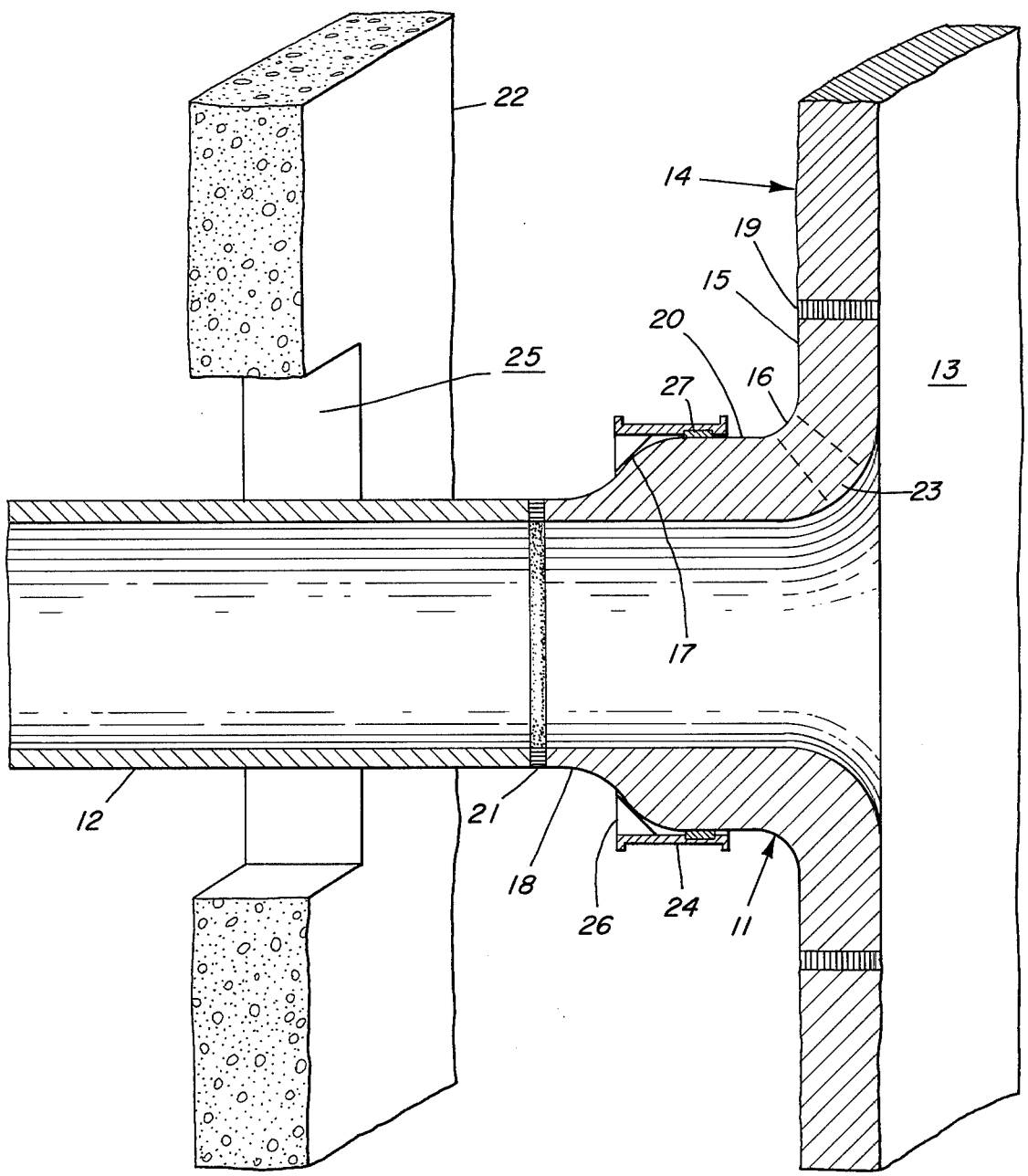
FIG. 1 is a vertical cross-section view of a portion of a vessel wall with a pipe and nozzle attachment.

Shown in FIG. 1 is a pipe attachment nozzle 11 connecting a pipe 12 to a curved wall 13 of a vessel 14. In a typical nuclear reactor pressure vessel, for example, the wall 13 is formed of welded-together plates of carbon steel in the order of 4–12 inches thick. The nozzle 11 is ordinarily a forging of carbon steel with a large diameter flange-like inner end 15, and inner radius or curved portion 16, a generally cylindrical body portion 20, an outer knee portion 17, and a small diameter outer end 18. The pipe 12, which may range in diameter from about 4 inches to about 28 inches may be formed of stainless steel for nuclear reactor system use.

The nozzle 11 is attached at its inner end 15 to the vessel wall 13 by a weld 19 and at its outer end 18 to the pipe 12 by a weld 21.

The vessel 14 is ordinarily surrounded by a cylindrical shield wall 22, constructed, for example, of concrete and formed with an opening or port 25 to provide a passage or penetration for the pipe 12 and to allow access to the region of the nozzle 11. (A layer of insulating material, not shown, is usually placed between the vessel 14 and the shield wall 22.)

It is desirable to examine three separate regions of the pipe-nozzle-vessel connection, namely, the region of the welds 19 and 21 and the region of the inner radius 16 (indicated by dashed lines as a region 23) which is a region of relatively high stress. It is further desirable that the inspection apparatus rapidly can be installed and removed (in the order of 10 minutes or less) to avoid undue human exposure, for example, to the radio activity emanating from a nuclear reactor pressure vessel and its adjacent attachments.

To provide a support and guide for the inspection vehicle a circular, U-shaped, removable track 24 adapted to be mounted on the outer knee portion 17 of the nozzle 11 is provided. To provide removability, the track 24 is formed in two or more segments. These segments may be fitted with alignment pins or formed with mating tongues and grooves at their ends (see FIG. 2) and/or interconnected by suitable hinges, resilient hasps or the like. The track 24 is fitted with a plurality of spaced, triangular support and locating members 26 secured, as by welding, to the track 24, the edges of the members 26 having an angle and shape conforming to the surface of the knee portion 17. The members 26 assure that the track can be reinstalled in the same position on the nozzle each time the nozzle is examined. The track 24 is held securely in place on the nozzle 11 by a plurality of spaced permanent magnets 27 attached to the track 24.

Figure 2:
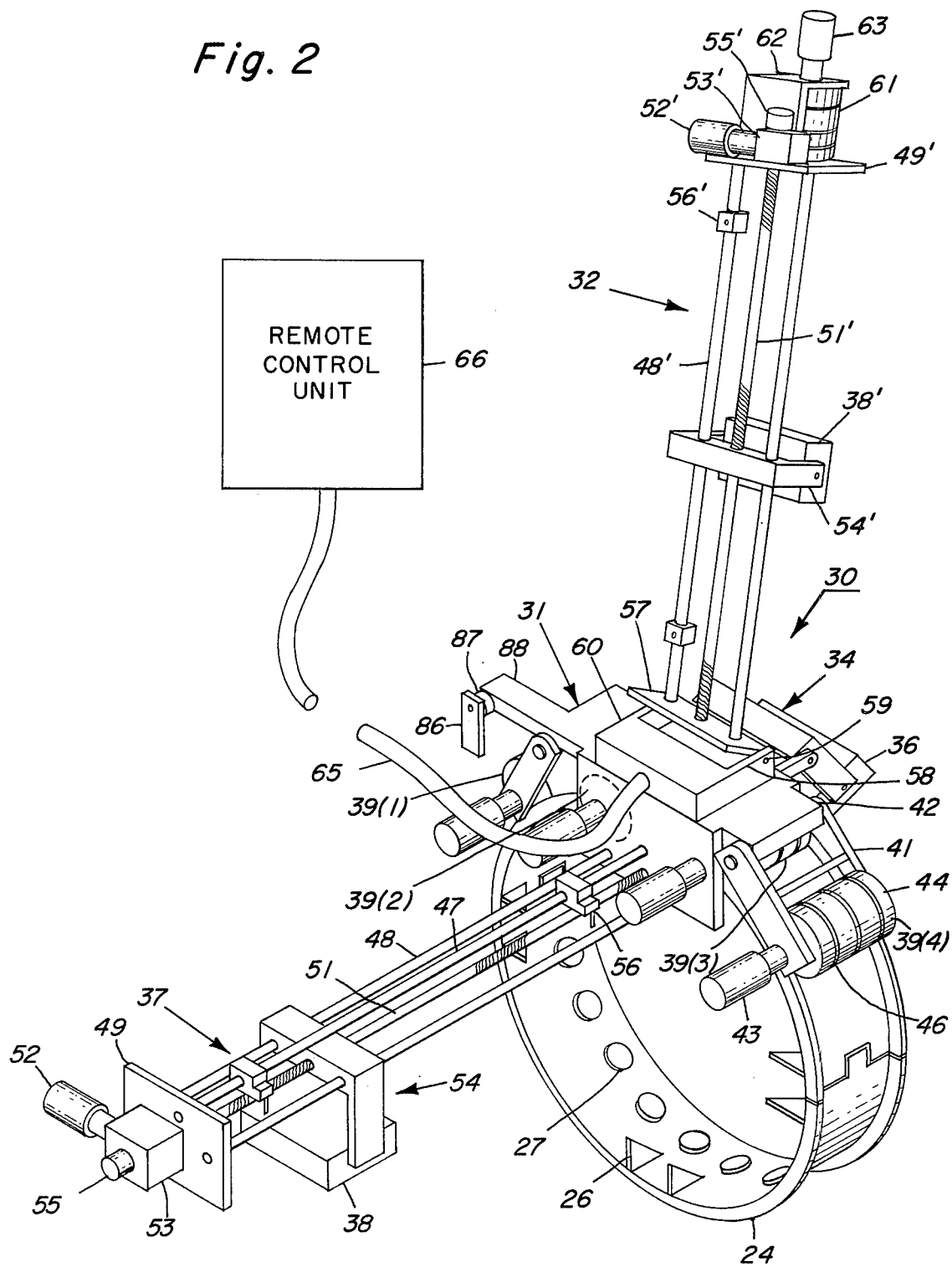
FIG. 2 is a perspective view of the nozzle inspection apparatus.

A nozzle inspection vehicle 30 in accordance with the invention is illustrated in FIG. 2. The vehicle 30 comprises a frame 31 (preferably formed of a non-magnetic material such as aluminum), an inner arm 32 carrying an inner transducer block 38' for scanning the vessel-to-nozzle weld 19, an intermediate arm 34 carrying a transducer block 36 for scanning the inner radius region 23 and an outer arm 37 carrying a transducer block 38 for scanning the nozzle-to-pipe weld 21.

The frame 31 is removably supported on the track 24 by a plurality of in-line wheels 39(1)–39(4). The inner wheels 39(2) and 39(3) are journalled for rotation in the U-shaped portion of the frame 31. The outer wheels 39(1) and 39(4) are journalled for rotation in frames 41, the frames 41 being pivotally attached to end extensions 42 of the vehicle frame 31.

The wheels 39(1) – 39(4) are driven by respective gear-head reversible electric motors 43 by which the vehicle 30 may selectively and remotely driven around the track 24.

To provide removable adherence of the vehicle 30 to the track 24, the track 24 is formed of a material having low magnetic reluctance, such as iron or steel, and the wheels 39(1) – 39(4) contain permanent magnets and are formed of a plurality of annular pole pieces 44 spaced by relatively thin spacers or washers 46 formed of non-magnetic material such as aluminum. Adjacent pole pieces 44 are oppositely poled so that strong magnetic fields are developed across the spacers 46 and hence through the track 24.

The outer arm 37 is attached to the frame 31 in cantilever fashion by a support rod 47 and a pair of support and guide rods such as rod 48 connected between the frame 31 and an end plate 49. A drive screw 51 is supported for rotation between the frame 31 and end plate 49 and is selectively driven by a reversable electric motor 52 (which may be a stepping motor) through a gear box 53. The transducer block 38 is pivotally and resiliently attached to a carriage 54 which is slidably supported on the guide rods 48 and driven by the drive screw 51. Thus by remote and selective actuation of the drive or stepping motor 52, the carriage 54 and hence the transducer block 38 can be moved back and forth across the nozzle-to-vessel weld 18. (Further details of carriage 54 and transducer block 38 are given hereinafter with reference to FIG. 3).

Suitable limit switches 56 can be adjustably mounted, for example, on support rod 47, to engage carriage 54 and stop or reverse the drive motor 52 at selected limits of travel.

A suitable rotation encoder 55 is coupled to provide a remote indication of the rotation of drive screw 51 by which the position of the carriage 54 on the arm 37 can be remotely determined.

The inner arm 32 is similar in most respects to the outer arm 37 described above. The arm 32 includes a pair of guide rods 48' connected between outer end plate 49' and an inner end plate 57. A drive screw 51' is supported for rotation between these end plates and is driven by a reversable motor 52' through a gear box 53'. Slidably mounted on the guide rods 48' and driven by the screw 51' is a carriage 54' which supports the inner transducer block 38' whereby the transducer block 38' may be moved back and forth across the vessel-to-nozzle weld 19. (Limit switches 56' adjustably mounted on guide rod 48' may be provided to determine limits of travel of carriage 54' and a rotation encoder 55' provides a remote indication of rotation of drive screw 51' and hence of the position of carriage 54'.) (Further details of the carriage 54' and transducer block 38' are described hereinafter with reference to FIG. 3)

To allow maintenance of constant spacing between the outer end of arm 32 and the vessel wall 13, the arm 32 is pivotally attached to the vehicle frame 31 by a bracket 58 and pivot pins 59. To maintain the arm 32 in its spaced position with respect to the vessel wall, a magnetic wheel 61 which may be similar to the vehicle wheels 39, is provided. The wheel 61 is supported for rotation in a frame 62 attached to the end plate 49', preferably by a pivotal connection. A reversible, geared electric drive or stepping motor 63 may be provided to drive the wheel 61 in synchronizm with the vehicle wheels 39(1) – 39(4).

To scan the inner radius area 23 (FIG. 1) the intermediate arm 34 comprises the transducer block 36 carried by a bracket secured to the frame 31 of the vehicle 30. Further details of the arm 34 are described hereinafter with reference to FIG. 4.

To provide an indication of the azimuth or attitude of the vehicle 30 and hence an indication of the position of the vehicle on the track 24, a pendulum 86 is provided. The pendulum arm is fixed to the movable element of a suitable position encoder 87, such as a potentiometer, the latter being supported on a bracket 88 extending from the vehicle frame 31.

An enclosure 60 mounted on the frame 31 is provided as a housing for terminal boards, relays, preamplifiers and the like and as a terminus for a remote control cable 65. The cable 65 contains the necessary electrical power, control and signal conductors. It also includes a flexible tube for providing a suitable coupling fluid (such as water) to the various acoustic signal transducers. For clarity of the drawing, the connections from cable 65 to the various devices on vehicle 30 are not shown. At its remote end the cable 65 is connected to suitable well-known supply, control, signal generating, receiving, processing, display and recording apparatus indicated schematically as a remote control unit 66.

Figure 3:
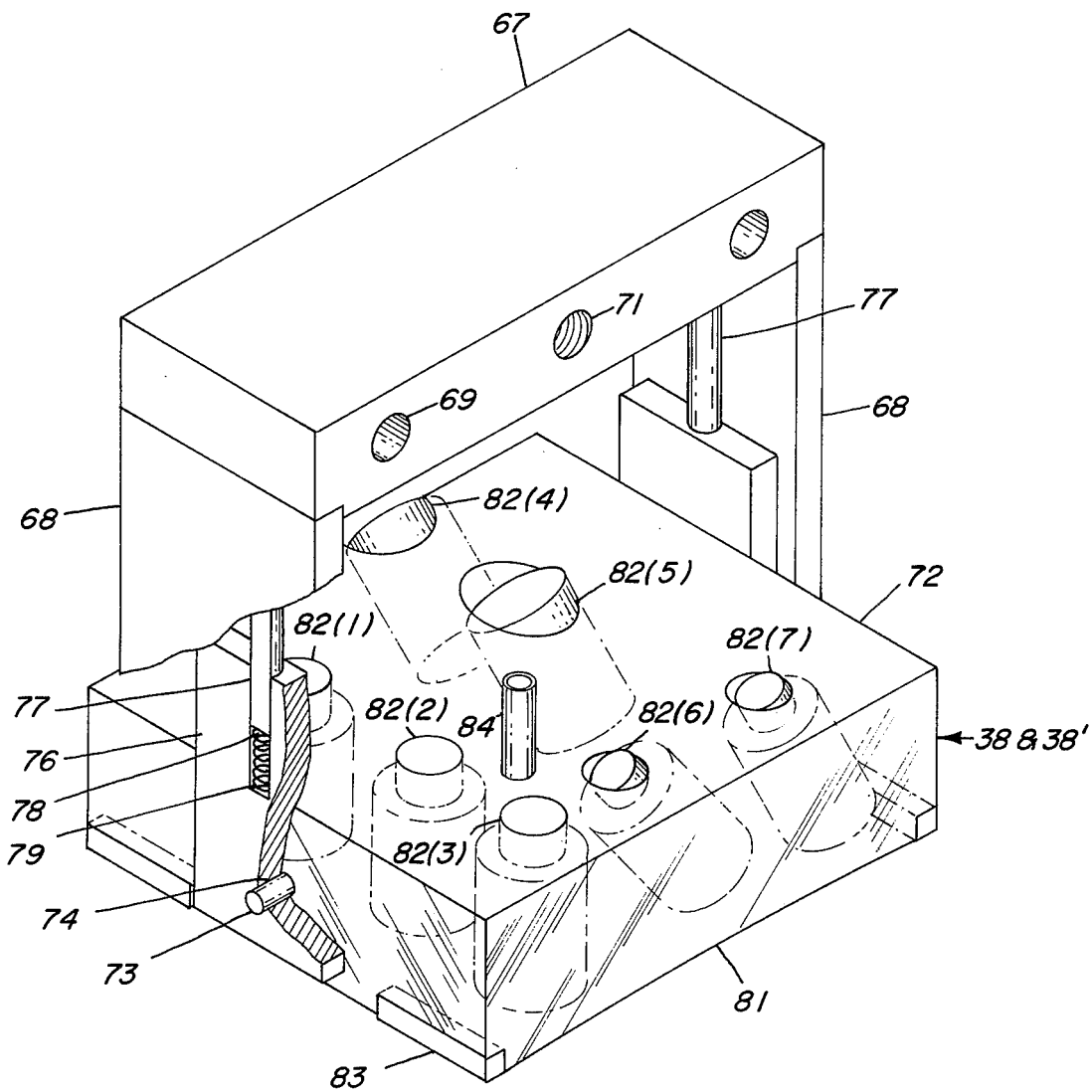
FIG. 3 is a perspective view of the outer and inner transducer blocks and carriages.

Transducer blocks 38 and 38' and their carriages 54 and 54' are shown in FIG. 3. Since these blocks and carriages are similar, to avoid duplication of drawing, the features of both are shown herein and the differences will be explained.

The carriages 54 and 54' include a transverse member 67 to which is attached side members 68 to thus form an inverted U-shaped carriage. The member 67 is formed with holes 69 through which the guide rods 48 (FIG. 2) extend. Holes 69 may be fitted with suitable bushings (not shown). The member 67 is also formed with a hole 71 which may be threaded or fitted with a threaded bushing or nut to receive the drive screw 51 (FIG. 2).

The transducer blocks 38 and 38' include a body 72 formed of a non-metallic material such as a suitable plastic. The body 72 is pivotally attached to the carriage 54 by an arrangement which also allows limited relative movement between the carriage and the transducer block. This arrangement includes a pair of pivot pins, such as a pivot pin 73, secured to an extending from opposite sides of the body 72. The pins 73 are journalled in bores 74 in a pair of connecting blocks 76.

Fixed to the inside surfaces of the side members 68 are respective guide bars 77 and the connecting blocks 76 are formed with mating grooves 78 by which the guide bars 77 are slideably engaged. For the carriage 54 and transducer block 38, a pair of coil springs, such as a spring 79, are placed in the grooves 78 between the guide bars 77 and the connecting blocks 76 by which the transducer block 38 is urged away from the carriage 54 to thereby maintain the face 81 of the transducer block in contact with nozzle outer end and pipe 12.

Fitted in cavities in the body 72 of the transducer block is a plurality of suitable transducers 82(1) – 82(7). These transducers are well-known devices for transmitting signals such as acoustic signals, into the metal under examination and for receiving reflected signals therefrom.

As shown in FIG. 3, transducers 82(1), 82(2) and 82(3) are mounted perpendicular to the face 81. Thus, for example, in examining the weld seam 21 (FIG. 1) one of these transducers can be used to examine the base metal of pipe 12, another can be used to examine the base metal of the nozzle outer end 18 while the other can be used for thorough examination of the weld 21. Transducers 82(4) and 82(5) are oriented at two different angles (for example 45° and 60°) from the face 81 in the direction of travel of the block 38 while the transducers 82(6) and 82(7) are oriented at different angles transverse to the direction of travel of the block 38. Thus transducers 82(4) – 82(7) can be used to examine the weld from two different directions at two different angles. In the transducer block 38' one of the transducers 82(1) – 82(3) can usually be omitted for examination of the vessel and nozzle inner end base metal since ordinarily they are both formed of similar metal, namely, carbon steel. The illustrated transducer arrangement is representative. Other suitable transducer arrangements can be used with the described inspection device as required.

For use in the inner arm 32, to assure close contact between the transducer block 38' and the vessel wall 13 and nozzle inner end 15 (and hence good coupling of the transducers), the body 72 may be fitted, at the corners of the face 81, with permanent magnets 83. In this case the springs 78 may be omitted. However, the magnets 83 are not effective for use in the transducer block 38 if the pipe 12 (FIG. 1) is formed of non-magnetic stainless steel.

The transducer blocks 38 and 38' are also provided with a tubular fitting 84 fixed to the body 72 by which a suitable acoustic signal coupling fluid (for example, water) may be fed through suitable channels (not shown) in the body 72 to the faces of the transducers 82(1) – 82(7).

Additionally, the face 81 of the body 72 of the transducer block 38 may be formed with a suitable curvature for conformance with the curved surface of pipe 12 and nozzle outer end 18.

Figure 4:
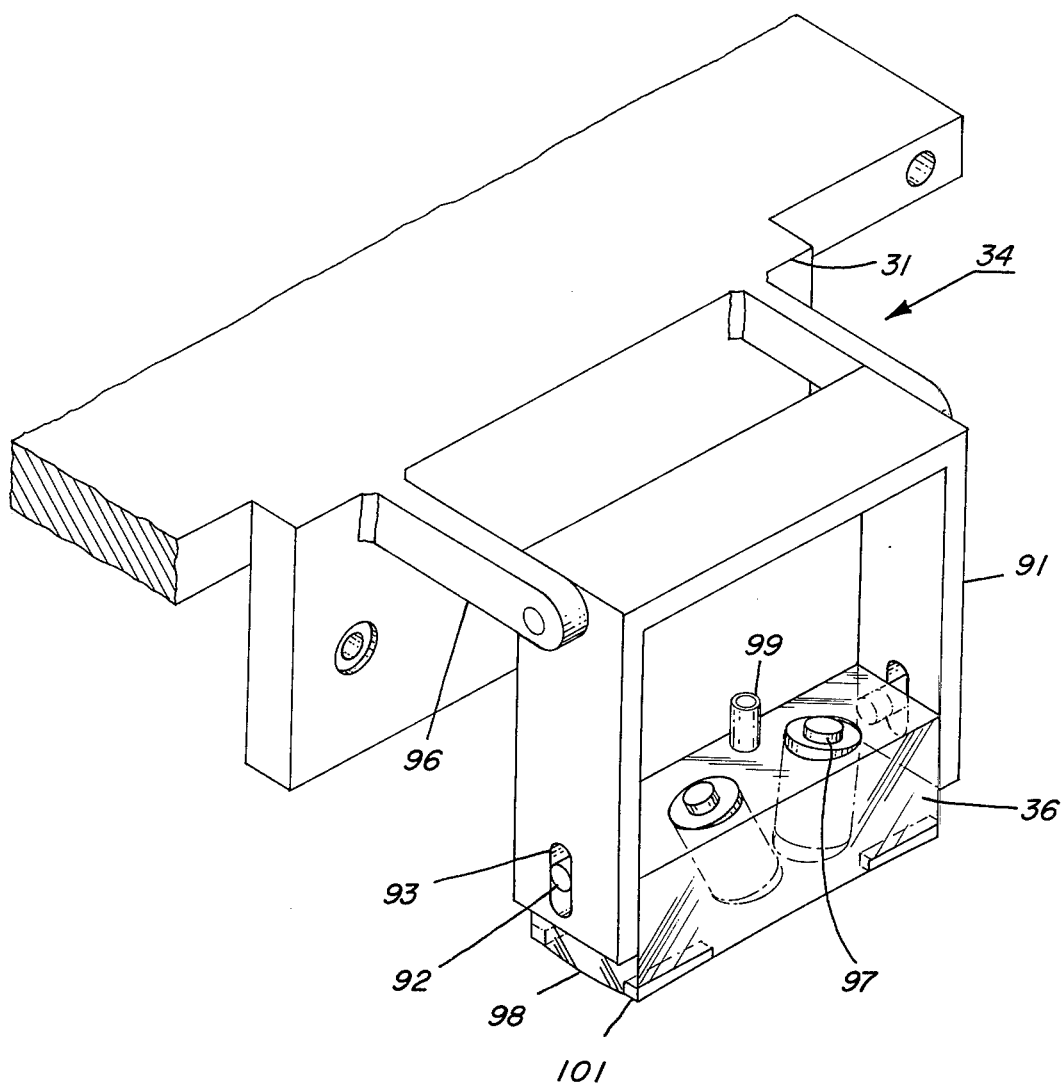
FIG. 4 is a perspective view of the intermediate arm.

The intermediate arm 34 is shown in greater detail in FIG. 4. The transducer block 36 is attached to a U-shaped carriage member 91 by pins 92 fixed to and extending from opposite sides of the block 36. The pins 92 engage slots 93 in the sides of the carriage 91 by which limited movement of the block 36 toward and away from the carriage 91 is allowed as the block 36 is moved over the curved or inner radius surface 16 of the nozzle 11 (FIG. 1).

The carriage 91 is pivotally attached to the vehicle frame 31 by brackets 96.

The transducer block 36 is fitted with a pair of suitable acoustic signal transducers 97 oriented at angles with respect to the face 98 of the block 36, the selected angle of orientation being suitable for examination of the inner radius region 23 of the nozzle 11.

A tubular fitting 99 is provided for attachment to a tube or hose for supplying a coupling fluid, through passages in block 36 (not shown), to the faces of the transducers 97. Permanent magnets 101 are fixed to the four corners of the transducer block face 98 to maintain the face 98 in close contact with the nozzle 11 and hence assure good transducer coupling. The face 98 of the transducer block 36 is preferably formed with suitable curvature to match the curvature of the outer surface of the inner radius or curved portion 16 of the nozzle 11.

(It is contemplated that separate tracks 24 and separate transducer blocks 36 and 38 will be provided for the different sizes of nozzles and pipes to be examined.)

It is contemplated that the transducers carried by the transducer blocks 36, 38 and 38' are operated in the well known "pulse-echo" manner, that is, each transducer operates as both a transmitter of pulses of acoustic signal and as a receiver of reflections back to the transducer of such signals. (As is well known, flaws or discontinuities in the metal under examination may be detected by the time and nature of the reflected signals.)

A suggested method of operation of the nozzle inspection apparatus is as follows: starting from a known location of the vehicle 30 on the track 24 (as indicated by the pendulum operated encoder 87) and a known location of the carriages 54 and 54' on the outer and inner arms (as indicated by the encoders 55 and 55'), the carriages 54 and 54' (and hence the transducer blocks 38 and 38') are moved in discrete steps along their respective arms across the welds 19 and 21. At each such step, the transducers are sequentially pulsed with an acoustic signal (for example, of a frequency of 2.25 MHz) and the reflected signals from these pulses are received processed and recorded in known manner.

After the carriages 54 and 54' have been thus stepped the desired distances to one side or the other of the welds 19 and 21, the drive motors 43 of the vehicle wheels (and motor 63 of the inner arm) are actuated to drive the vehicle a predetermined step along the track 24 to thereby present another (preferably overlapping) scanning path for the transducers of transducer blocks 38 and 38'. The carriages 54 and 54' are then moved in discrete steps in the opposite direction across the welds 19 and 21 and the transducers are pulsed etc.

The transducers of the intermediate arm transducer block 36 are also pulsed and any reflected signals therefrom received and recorded at least once for each position of the vehicle 30.

In this manner a complete examination of the welds 19 and 21 and the inner radius region 23 can be accomplished.

Thus what has been described is readily installable and removable apparatus which can be remotely operated to examine the connection of a pipe to vessel.

What is claimed is:

1. Remotely operable apparatus for inspecting the connection of a pipe to the wall of a vessel, said connection being formed by an attachment nozzle, said nozzle having a flange-like inner end welded by an inner weld within an aperture in said vessel, a generally cylindrical body portion extending outward from said vessel, a curved inner radius portion between said inner end and said body portion, and an outer end portion welded by an outer weld to said pipe, said apparatus comprising: a circular track positioned around said body portion of said nozzle, said track being formed of magnetic material; a vehicle adapted to run on said track said vehicle including a frame, a pair of wheels journalled in said frame, said wheels including permanent magnet means for adherence of said wheels to said track, selectively operable drive means for said wheels for driving said vehicle around said track, an outer arm attached to said frame and extending therefrom generally parallel to said pipe, a first carriage mounted on said outer arm, said outer arm including first guiding means for guiding said first carriage back and forth along said arm, a first transducer block including at least one transducer for transmitting and receiving inspection signals, first attachment means for attaching said first transducer block to said first carriage, said outer arm including selectively operable drive means engaging said carriage for moving said first transducer block back and forth along said first guiding means across said outer weld; an inner arm attached to said frame and extending therefrom generally parallel to said wall of said vessel, a second carriage mounted on said inner arm, said inner arm including second guiding means for guiding said second carriage back and forth along said arm, a second transducer block including at least one transducer for transmitting and receiving inspection signals, and second attachment means for attaching said second transducer block to said second carriage, said inner arm including selectively operable drive means engaging said second carriage for moving said second transducer block back and forth along said second guiding means across said inner weld.

2. Apparatus according to claim 1 further including an intermediate arm attached to said frame and extending therefrom toward said curved portion of said nozzle, said intermediate arm including a bracket attached to said frame, a third carriage pivotally attached to said bracket, a third transducer block including at least one transducer for transmitting and receiving inspection signals, third attachment means for attaching said third transducer block to said third carriage, said third transducer block having a face engaging the outer surface of said curved portion of said nozzle for examination of said curved inner radius portion of said nozzle.

3. Apparatus according to claim 1 wherein said first attachment means provides limited relative movement between said first carriage and said first transducer block and included resilient means urging said first transducer block in a direction away from said first carriage for maintaining a face of said first transducer block in contact with the surface of said pipe and the surface of said outer end portion of said attachment nozzle.

4. Apparatus according to claim 3 wherein said face of said first transducer block is formed with a curvature substantially conforming with the curvature of said surfaces of said pipe and said outer end portion of said attachment nozzle.

5. Apparatus according to claim 1 wherein said second attachment means provides limited relative movement between said second carriage and said second transducer block and wherein said second transducer block includes a face and at least one permanent magnet embedded in said face for slidable adherence of said second transducer block to the surface of said vessel wall and the surface of said inner end portion of said nozzle.

6. Apparatus according to claim 2 wherein said third attachment means provides limited relative movement between said third carriage and said third transducer block and wherein said third transducer block includes a face and at least one permanent magnet embedded in said face for slidable adherence of said third transducer block to the outer surface of said curved portion of said nozzle.

7. Apparatus according to claim 6 wherein said face of said third transducer block is formed with a curvature substantially conforming with the outer surface of said curved portion of said nozzle.

8. Apparatus according to claim 1 wherein an end of said inner arm is pivotally attached to said frame and the other end of said inner arm is supported by an inner arm wheel, said wheel containing permanent magnets for adherence of said wheel to said wall of said vessel.

9. Apparatus according to claim 8 including a selectively operable electric drive motor for said inner arm wheel.

10. Apparatus according to claim 1 further including a frame pivotally attached to one end of said vehicle frame and a third wheel journalled in said frame for rotation on said track, said third wheel containing permanent magnet means for adherence of said third wheel to said track.

11. Apparatus according to claim 10 further including another frame pivotally attached to the other end of said vehicle frame and a fourth wheel journalled in said frame for rotation on said track, said fourth wheel containing permanent magnet means for adherence of said fourth wheel to said track.

12. Apparatus according to claim 11 including respective selectively operable electric drive means for said third and fourth wheels.

13. Apparatus according to claim 12 wherein said pair of wheels and said third and fourth wheels are formed of a plurality of spaced annular pole pieces energized by permanent magnets to form opposite magnetic poles at adjacent ends of said pole pieces.

14. Apparatus according to claim 1 further including a pendulum arm pivotally attached to said vehicle and means operated by said pendulum arm for indicating the position of said pendulum arm with respect to said frame of said vehicle.

15. Apparatus according to claim 1 wherein said selectively operable drive means for said first carriage includes a drive screw engaging said first carriage, selectively operable electric drive means for rotating said drive screw, and encoder means coupled to said drive screw for indicating rotation thereof.

16. Apparatus according to claim 15 further including limit means mounted on said outer arm for controlling said drive means to limit travel of said first carriage along said outer arm.

17. Apparatus according to claim 1 wherein said selectively operable drive means for said second carriage includes a drive screw engaging said second carriage, selectively operable electric drive means for rotating said drive screw, and encoder means coupled to said drive screw for indicating rotation thereof.

18. Apparatus according to claim 17 further including limit means mounted on said inner arm for controlling said drive means to limit travel of said second carriage along said inner arm.

19. Apparatus according to claim 1 wherein said track is segmented for removable attachment to said body portion of said nozzle.

20. Apparatus according to claim 19 wherein said segments of said track are fitted with a plurality of permanent magnets for removable adherence of said segments to said body portion of said nozzle.

21. Apparatus according to claim 20 wherein said track segments are formed with mating alignment at their ends.

22. Apparatus according to claim 1 wherein said first transducer block includes a face for contacting the surface of said pipe and said outer end portion of said nozzle, said first transducer block including at least two acoustic signal transducers oriented substantially perpendicular to said face, at least two acoustic signal transducers oriented in a given direction at different angles to said face, and at least two acoustic signal transducers oriented in a direction substantially ninety degrees from said given direction and at two different angles to said face.

23. Apparatus according to claim 1 wherein said second transducer block includes a face for contacting the surface of said vessel wall and said inner end of said nozzle, said second transducer block including at least two acoustic signal transducers oriented substantially perpendicular to said face, at least two acoustic signal transducers oriented in a given direction at different angles to said face, and at least two acoustic signal transducers oriented in a direction substantially ninety degrees from said given direction and at two different angles to said face.

24. Apparatus according to claim 2 wherein said third transducer block includes at least two acoustic signal transducers oriented at different angles to said face of said third transducer block.

* * * * *